United States Patent
Sablone et al.

(10) Patent No.: US 12,065,278 B2
(45) Date of Patent: Aug. 20, 2024

(54) UNIT, APPARATUS AND METHOD FOR CUTTING A CHAIN OF ARTICLE

(71) Applicant: Fameccanica.Data S.p.A., San Giovanni Teatino (IT)

(72) Inventors: Gabriele Sablone, San Giovanni Teatino (IT); Antonio Gallucci, San Giovanni Teatino (IT)

(73) Assignee: Fameccanica.Data S.p.A.

( * ) Notice: Subject to any disclaimer, the term of this patent is extended or adjusted under 35 U.S.C. 154(b) by 0 days.

(21) Appl. No.: 18/177,664

(22) Filed: Mar. 2, 2023

(65) Prior Publication Data
US 2023/0278743 A1    Sep. 7, 2023

(30) Foreign Application Priority Data
Mar. 4, 2022   (IT) .................. 102022000004127

(51) Int. Cl.
| | | |
|---|---|---|
| *B65B 61/06* | (2006.01) |
| *B65B 9/087* | (2012.01) |
| *B65B 51/26* | (2006.01) |
| *A61F 13/551* | (2006.01) |

(52) U.S. Cl.
CPC .............. *B65B 61/06* (2013.01); *B65B 9/087* (2013.01); *B65B 51/26* (2013.01); *A61F 13/551* (2013.01)

(58) Field of Classification Search
None
See application file for complete search history.

(56) References Cited

U.S. PATENT DOCUMENTS

| | | | |
|---|---|---|---|
| 6,050,927 A | | 4/2000 | Harrod |
| 2019/0161312 A1 | * | 5/2019 | Meyerhans .............. B26D 9/00 |

FOREIGN PATENT DOCUMENTS

| | | |
|---|---|---|
| IT | 201900015650 A1 | 3/2021 |
| JP | 2012066934 A | 4/2012 |
| WO | 2013038310 A1 | 3/2013 |

OTHER PUBLICATIONS

Search Report dated Oct. 22, 2022. 7 pages.
Japanese Office Action. 3 pages.

* cited by examiner

*Primary Examiner* — Tanzim Imam
(74) *Attorney, Agent, or Firm* — RMCK Law Group PLC

(57) ABSTRACT

A cutting unit configured to make segments of consecutive articles from a continuous chain of articles, where the segments of consecutive articles have a desired number of articles in each segment of articles.

10 Claims, 4 Drawing Sheets

UNIT, APPARATUS AND METHOD FOR CUTTING A CHAIN OF ARTICLE

CROSS-REFERENCE TO RELATED APPLICATION

This application claims priority to Italian Patent Application No. 102022000004127 filed Mar. 4, 2022. The disclosure of the above application is incorporated herein by reference in its entirety.

FIELD OF THE INVENTION

The present invention relates in general to the packaging sector and specifically concerns flow-pack packaging.

More precisely, the invention relates to a transversal cutting unit which can be used for the packaging of sanitary-absorbent articles, such as for example diapers, diaper-panties, feminine sanitary towels, etc.

DESCRIPTION OF THE PRIOR ART

Flow-pack packaging is one of the most popular systems for packaging a large variety of consumer products.

In flow-pack packaging systems, a continuous packaging film, typically of plastic material, is unwound from a reel and is folded into the shape of a continuous tubular member that surrounds the products to be packaged and advances in a machine direction together with the flow of products to be packaged. The continuous tubular member of packaging material is closed by means of a continuous longitudinal seal that joins the opposite longitudinal edges of the packaging film and by means of transverse seals spaced apart from each other in the machine direction that seal the continuous tubular member at opposite sides with respect to the products that must be included in a single package.

A flow-pack packaging machine typically comprises:
- a horizontal conveyor configured to advance a flow of products along a longitudinal direction,
- an unwinding unit configured to feed a continuous packaging film,
- a stationary forming device configured to fold the packaging film in the form of a tubular element that surrounds the products to be packaged,
- a longitudinal welding assembly located downstream of the forming device and configured to weld together opposite longitudinal edges of the packaging film,
- a transverse welding assembly configured for transversally welding the tubular element formed by the film of packaging material, and
- a cutting element to separate the products.

In accordance with a per se known technique, the packaging of absorbent sanitary articles, such as, for example, diapers, is achieved by wrapping the folded articles in a continuous film generally of polyethylene, by means of a suitable folding nozzle. The individual articles are transported in a machine direction within the continuous film that surrounds them. In the known solution, a welding station is arranged to seal the ends of the single package being created and, at the same time, a blade integrated in the same welding station separates the individual packages from each other. In a subsequent step of the method, the single package is carried to the step that is useful for multi-product packaging in larger bags.

Known solutions envisage that the packaging machine is configured to produce strips of single packages, each including one or more products, wherein the individual packages are connected to each other and pre-engraved along the transverse sealing, to facilitate subsequent detachment of the single package.

The present invention starts from the desire to make a cutting unit, an apparatus, and a relative method, arranged to make both a plurality of individually separated packages, and continuous and pre-engraved strips of individual packages, with the possibility of carrying out an automatic separation of the packages every n articles, where n varies according to production requirements.

OBJECT AND SUMMARY OF THE INVENTION

The object of the present invention is to provide a device that satisfies the requirements indicated above.

According to the present invention, this object is achieved, by a cutting machine, an apparatus and a method having the characteristics forming the subject of claims 1, 5, 8. Preferred embodiments of the invention form the subject of the dependent claims.

The claims form an integral part of the disclosure provided here in relation to the invention.

BRIEF DESCRIPTION OF THE DRAWINGS

The present invention will now be described in detail with reference to the attached drawings, given purely by way of non-limiting example, wherein.

DETAILED DESCRIPTION

Figure 1:
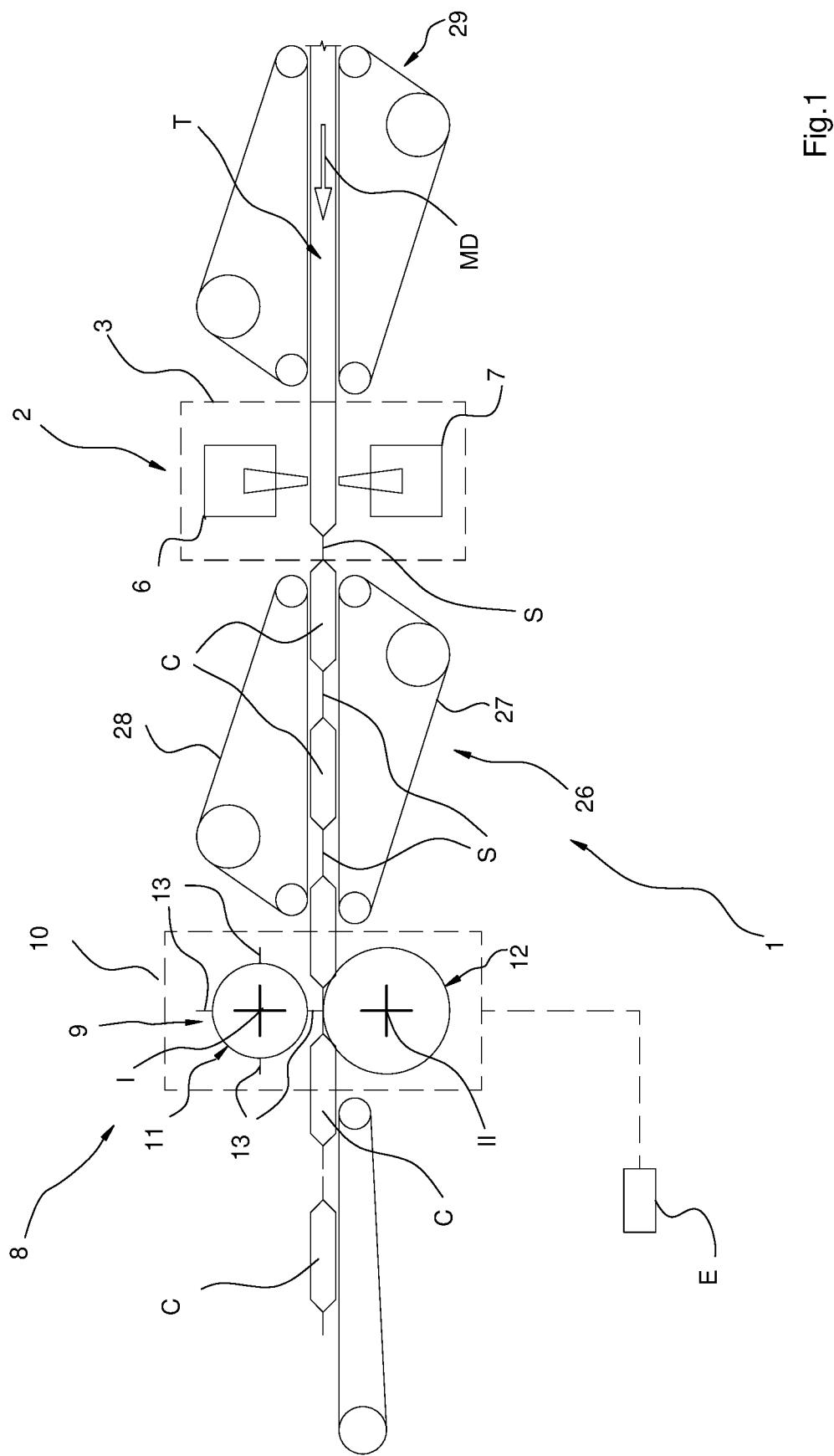
FIG. 1 is a schematic side view of a flow-pack packaging apparatus according to the present invention.
Figure 4:
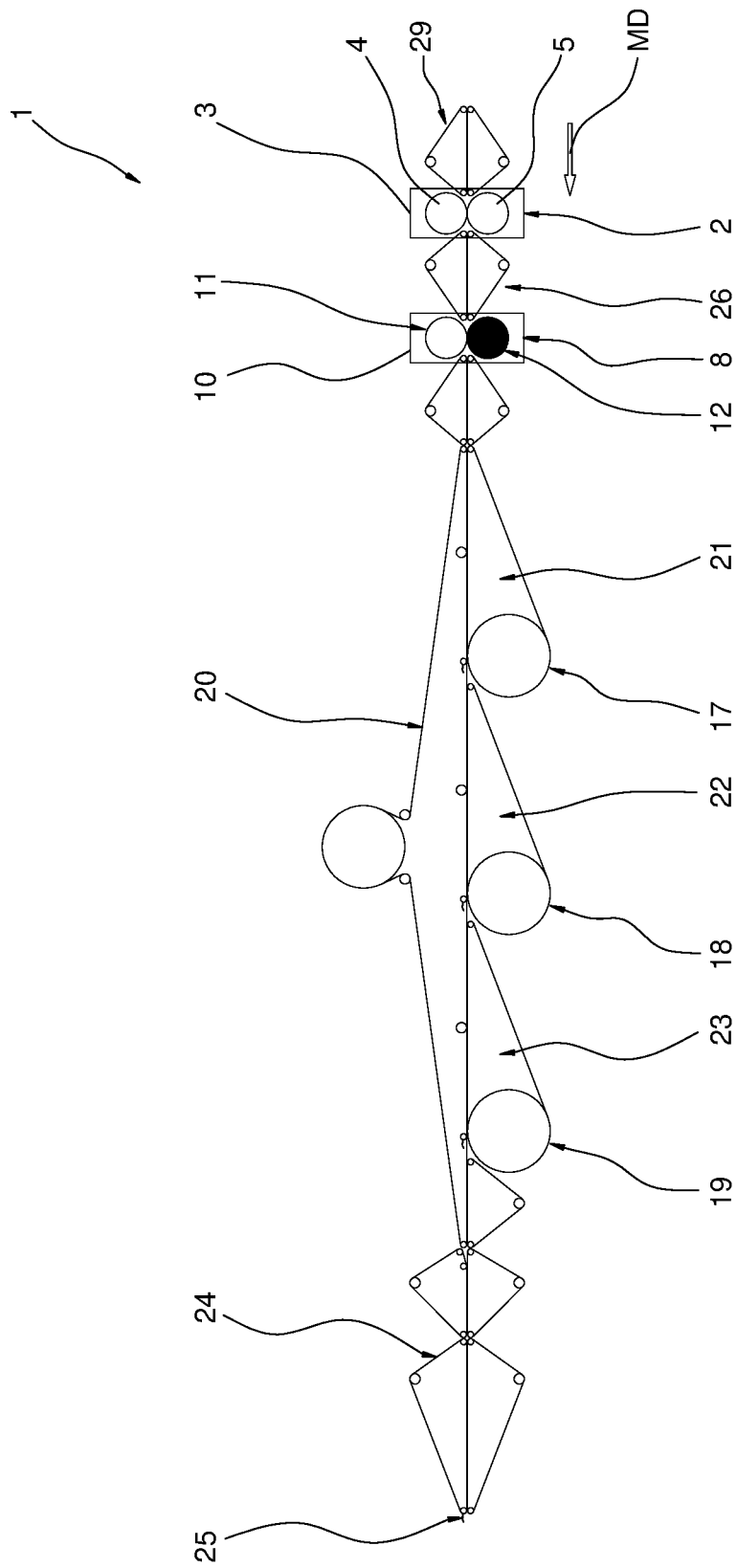
FIG. 4 is a schematic side view of an apparatus according to the invention, wherein additional operational operating steps are shown.

With reference to FIGS. 1, 4, numeral 1 indicates a packaging apparatus of the horizontal flow-pack type.

In a packaging apparatus intended to form packages of the type currently referred to as "flow-pack", a conveyor is configured to advance a flow of articles to be packaged along a machine direction MD. In accordance with a preferred embodiment, the apparatus 1 is arranged to advance the articles along a substantially horizontal direction.

In one or more embodiments, the apparatus 1 is arranged to package a flow of absorbent sanitary articles, such as for example diapers, diaper-panties, feminine sanitary towels, etc.

The packages C are formed by arranging a continuous flow of articles fed to an inlet end of the apparatus 1 and by a continuous packaging film fed by an unwinding assembly of any known type.

According to widely known criteria, starting from the continuous film, a continuous envelope T of substantially tubular shape is formed, which surrounds the articles to be packaged, by means of a forming device configured to fold the continuous packaging film.

The continuous envelope T is advanced towards a longitudinal sealing station whose function is essentially to seal the longitudinal edges of the continuous envelope between two consecutive articles. According to a solution known per se, the sealing station may comprise a glue applicator designed to apply a layer of adhesive material along the longitudinal edges of the envelope T to be sealed.

FIG. 1 illustrates a preferred embodiment of an apparatus 1 according to the invention. In FIG. 1, the articles are transported along the machine direction MD from right to left. FIG. 1 does not show the details relating to the unwinding assembly, the forming device and the longitudinal sealing station, as these details may be made according to the prior art.

In accordance with a further characteristic of the invention, the continuous tubular envelope T is advanced by means of automated transport means 29 towards a transversal welding unit 2 whose function is essentially to flatten the continuous envelope T in the spaces comprised between two consecutive articles, forming welding areas S in these spaces intended to hermetically separate the articles constituting a single package.

As illustrated in FIG. 4, the transversal welding station 2 may be composed of a support structure 3 where a pair of counter-rotating rollers is installed, in particular, a welding roller 4 and a contrasting roller 5. The rollers 4,5 are actuated, in a known way, for example, by a single motorization with the arrangement of transmission means, or by means of two independent motorizations constituted by two servomotors electronically controlled between them.

In one or more embodiments, the welding action is achieved with the combined application of pressure and heat. To this end, both the rollers 4, 5 have heating resistors and temperature control means mounted inside them (according to a per se known configuration).

In one or more embodiments, as in the one illustrated in FIG. 1, the transversal welding unit 2 comprises a first welding element 6 and a second welding element 7 movable with respect to each other according to a second straight direction perpendicular to the first machine direction MD, between an open position and a closed position. The welding elements 6,7 may be configured to carry out ultrasonic welding.

According to the invention, the apparatus 1 comprises a transversal cutting unit 8 that is separate and arranged downstream of the welding unit 2, with reference to the machine direction MD.

Figure 2:
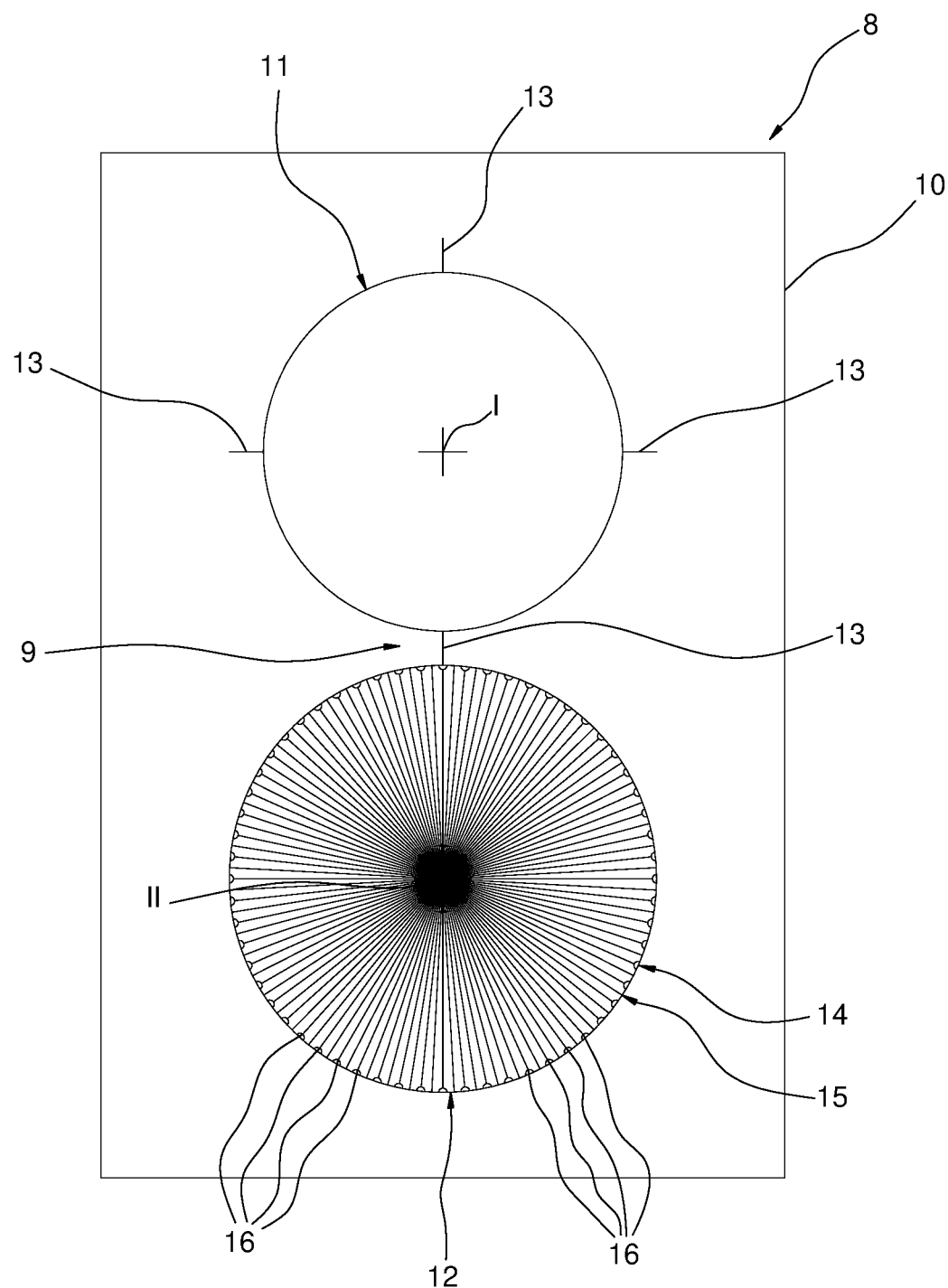
FIG. 2 is a cross-sectional view of a cutting unit according to a preferred embodiment.

As illustrated in FIGS. 1, 2, 4, the cutting unit 8 comprises a pair of active rotary elements 9 positioned at a respective side of the continuous envelope T, and configured to rotate around a respective axis I, II. In accordance with the example of horizontal packaging apparatus 1, the rotary elements are respectively positioned above and below the continuous envelope T.

In one or more embodiments, the transversal cutting unit 8 may comprise a support structure 10 on which the pair of active rotary elements 9 are mounted.

The pair of active rotary elements 9 essentially consists of a cutting roller 11 (or knife) and a contrasting roller 12 (or counter-knife) driven in rotation by motor means (not shown).

FIG. 2 is a schematic view on an enlarged scale illustrating a preferred embodiment of the transversal cutting unit 8. In accordance with the illustrated embodiment, the first rotary element (cutting roller 11) carries at least one cutting element 13 on its surface, to perform a cutting operation at a welded area S of the continuous envelope T, which advances along the welding unit 2 and cutting unit 8. Preferably, the cutting roller 11 has four cutting elements 13 spaced at 90° along the circumference of the cutting roller 11.

Again with reference to FIG. 2, the second active rotary element (contrasting roller 12), which acts as a contact surface for the cut, has a plurality of sections with grooves 14, alternating with a plurality of solid sections 15. As is evident from the following description and from the attached drawings, each section with grooves 14 has a plurality of hollow portions 16, each shaped so as to create a groove with respect to the continuous outer surface of the roller 12, while each solid section 15 has a regular continuous outer contact surface for cutting. The contrasting roller 12 may be made as a monolithic body with integrated hollow portions 16.

It should be noted that the sections with grooves and solid sections 14, 15 are alternated at a constant pitch along the circumference of the contrasting roller 12.

Therefore, during operation, each cutting element 13 cooperates with the contrasting roller 12 on a corresponding section with grooves or solid section 14, 15.

Thanks to the characteristics indicated above, during operation, when a cutting element 16 acts on a solid area—solid section 15—a clean cut is made between two consecutive articles, thus separating the packages C. Conversely, when a cutting element 16 acts on a region with grooves—section with grooves 14—an engraving is made between two consecutive articles, without separating the articles, so as to create a segment of a plurality of consecutive articles. A transversal engraving is therefore formed between two consecutive articles, designed to favor a subsequent separation of the articles. The segments may thus be made of a certain desired length (a certain number of consecutive engraved articles). Note that the expression "desired length" means that it is possible to make batches of segments of articles of one length and batches of segments of another length different from the previous one, for example, groups of segments of three articles and groups of segments of five articles.

As previously indicated, the rollers 11, 12 are driven in rotation by motor means not shown in the drawings. In accordance with the invention, the motor means comprise independent electronically-controlled servomotors connected, respectively, to the cutting roller and to the contrasting roller.

In accordance with an additional characteristic of the invention, the apparatus 1 comprises an electronic control device E (illustrated in FIG. 1) programmed to vary the phase between the cutting roller 11 and the contrasting roller 12. The expression "vary the phase" means a variation of the relative angular position between a cutting element 13 and a section with grooves/solid sections 14,15, during an operating cycle. In this way, it is possible to vary the frequency with which the contact of a cutting element 13 occurs with a solid section 15 and the contact of said cutting element 13 with a section with grooves 14, so as to vary pre-incision cuts and clean cuts of the continuous envelope T that wraps the articles, in a variable way according to the production requirements. In one or more embodiments, the control device E is programmed to automatically control the contrasting roller 12 in acceleration or deceleration with respect to the cutting roller 11, so as to vary the length of the segments of consecutive articles with engravings between one article and another. Thanks to these characteristics, article segments may be made of variable lengths without interrupting the production process. It should be noted that FIG. 1 illustrates an operating step of operation wherein the cutting unit is controlled to produce a plurality of articles with cut and separated packages C.

For correct operation, the cutting roller 11 must have a peripheral speed substantially equal to the feed speed of the continuous envelope T. The contrasting roller 12 will, instead, have a variable peripheral speed, substantially corresponding to a multiple integer of the pitch between the alternating sections 14, 15 and close to the feed rate of the packages through the cutting unit 8, to achieve the separation of the packages C or the continuous strip of pre-engraved packages C.

The description and attached drawings refer to a transversal cutting unit 8, and to a related apparatus 1, arranged to cut/engrave the continuous envelope T including a plurality of articles mutually spaced apart at a constant pitch. However, it should be noted that the invention is equally applicable for cutting/engraving applied directly to a continuous chain of articles still without any packaging envelope.

More generally, in the context of the overall apparatus 1, the electronic control device E is, furthermore, configured to synchronize the operation of the transversal welding unit 2 and of the cutting unit 8, so as to carry out the welding and the cutting (or pre-incision) of packages C in a single apparatus 1. In this regard, in one or more embodiments, as in the one illustrated in FIG. 1, a stabilization unit 26 of the packages C is interposed between said welding unit 2 and said cutting unit 8, comprising:

- a lower conveyor element 27 of continuous motorized loop type, having an active branch for conveying the packages C substantially aligned with the direction MD of the transit movement of the packages C, and
- a motorized upper conveyor element 28 having an active branch in contact with the transiting packages C.

In one or more embodiments, the operation of the forming of the packages C is continuous, as the envelope T may undergo variations in speed, but it never stops during operation to carry out the welding and cutting operations.

In a preferred embodiment, the transversal cutting unit 8 has rollers 11, 12, which are rotated in opposite directions. This causes a circular movement in opposite directions of the rollers 11, 12, which brings, each time, a cutting element 13 into contact with a section with grooves 14 or with a solid section 15, respectively, to carry out the pre-incision without separating the articles or the cut of the envelope E with separation.

As previously indicated, the alternating grooves and solid sections 14, 15 are arranged at a constant pitch along the circumference of the contrasting roller 12.

Figure 3:
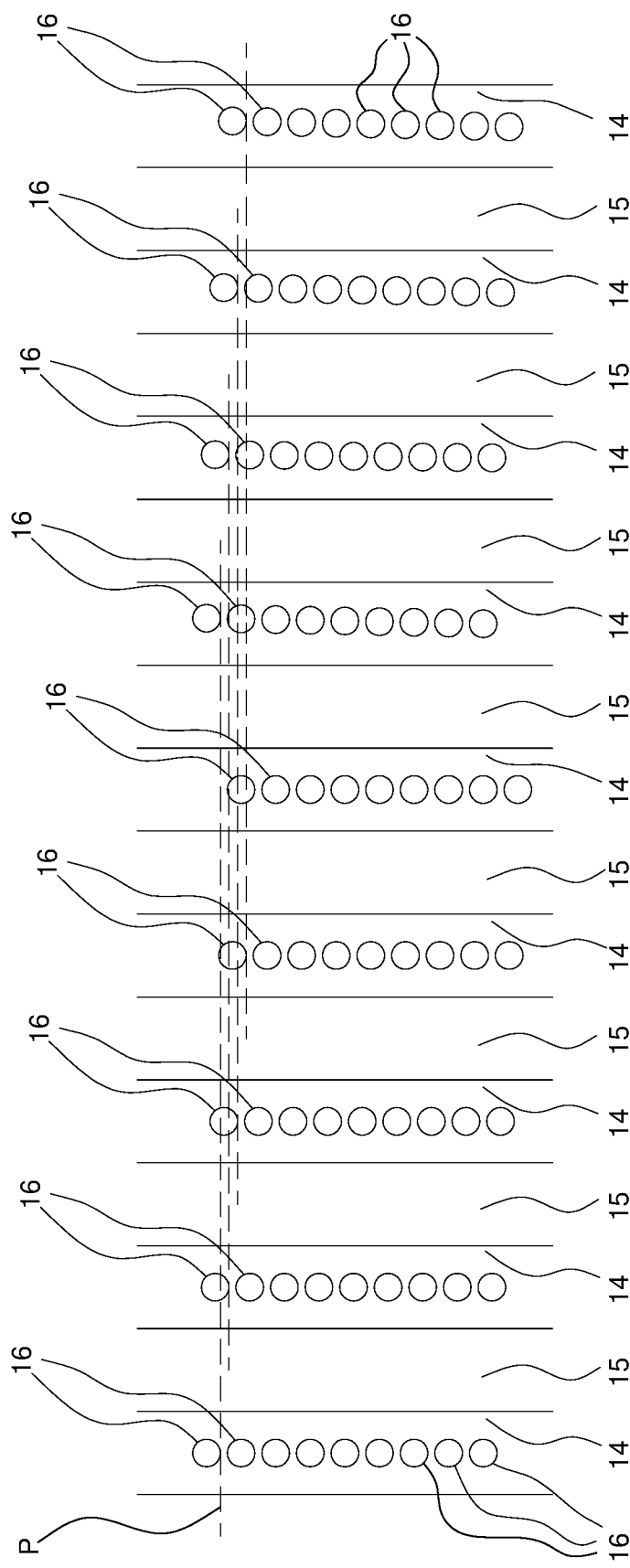
FIG. 3 is a plan view of some details of the previous Figure.

FIG. 3 shows a schematic view on an enlarged scale of the contrasting roller 12. For each section with grooves 14, a plurality of hollow portions 16 are provided, aligned along a transversal direction with respect to the machine direction MD, arranged to carry out the required pre-incision. Preferably, the hollow portions 16 are circular in shape.

In accordance with another preferred characteristic of the invention, the position of the hollow portions 16 varies from one section with grooves 14 to another, so that it does not come into contact with the cutting element 13 in the same way, so as to limit and make the wear of the cutting element 13 uniform. With reference to the embodiment illustrated in the plan view of FIG. 3, it should be noted that the rows of hollow portions 16 of the sections 14 are mutually misaligned along the axial direction of the sections 14. There is, therefore, a shift in position of the rows of hollow portions 16 between the sections 14 of the roller 12. This position deviation of the hollow portions 16 may be achieved in the order of 1-10 mm, according to different configurations.

In the configuration shown in FIG. 3, the position deviation is constant and progressive for a given number of sections 14. For example, a succession of n sections 14 may have a progressive deviation of about 1 mm. In other words, from a first to a second section 14 there is a deviation of 1 mm, and from the second section 14 to the third section 14 there is a further deviation of 1 mm. At the end of a first succession of n sections 14 with constant and progressive deviation, a second succession of n sections 14 shows the same arrangement of hollow portions 16 as the previous succession. In this regard, by way of example, the Figure shows a reference line P configured for indicating the constant and progressive deviation of the hollow portions 16 for a succession of five sections with hollows 14. In FIG. 3, this constant and progressive deviation of the hollow portions 16, which in this exemplifying case refers to a succession of five sections with grooves 14, is to be understood as defined by the distance between the centers of the further reference lines parallel to the reference line P.

According to a further configuration not shown, considering a succession of n sections 14, the deviation in position of the slots 16 between the sections 14 can be increasing from one section 14 to another (for example, from a first to a second section, deviation of 1 mm, and from the second section to a third section deviation of 2 mm).

Of course, the position deviation of the hollow portions 16 between the sections 14 may be achieved differently from what has been described above, provided that it is suitable for achieving the intended objects, i.e. creating the pre-incision effectively and limiting the wear of the cutting edges 13.

FIG. 4 illustrates a schematic side view of a preferred embodiment of an apparatus according to the present invention. According to a further characteristic of the invention, the apparatus 1 is configured to carry out an automatic sorting of the packages C produced.

In one or more embodiments, the apparatus 1 has a plurality of conveyor means 20, 21, 22, 23 configured for automatically transporting the strips of consecutive pre-engraved uncut packages C automatically towards respective evacuation points 17, 18, 19. Preferably, the apparatus 1 has at least three evacuation points 17, 18, 19 of the strips of packages C by means of the automatic activation of vacuum areas, to automatically sort the packages C towards certain collection points. These vacuum areas are made by vacuum conveyors of known type.

The function of the conveyors 20, 21, 22, 23 is to positively guide the strips of packages C towards the evacuation points 17, 18, 19 (for example, within a collection box accessible from the outside or onto a further belt to carry the packages C out of the overall dimensions of the apparatus 1, for subsequent collection and bagging). The conveyors 20, 21, 22, 23 may be alternatively activated, according to a predetermined cycle by means of a command signal sent by the control device E, to allow n strips of packages C of m products to be respectively transported towards a given evacuation point 17, 18, 19.

The conveyor means 20, 21, 22, 23 may comprise a plurality of lower belts 21,22,23, and an upper belt 20 configured for gripping the package portions C between their respective mutually facing surfaces. The upper belt 20 has a length substantially corresponding to that of the lower belts 21,22,23 in succession. Each lower belt 21,22,23 is arranged to guide the strips of products towards a respective evacuation point 17, 18, 19. As indicated above, the conveyors 20, 21, 22, 23 may comprise preferably sub-atmospheric pressure gripping means comprising a source of sub-atmospheric pressure.

In one or more embodiments, such as in the one illustrated in FIG. 4, the apparatus 1 comprises further transport means 24 arranged at the end of the line with respect to the evacuation points 17, 18, 19, to transport the separate cut packages C beyond the aforesaid evacuation points 17, 18, 19 in an end-of-line point 25 for picking up (for example, for the bagging of packages of larger dimensions).

Thanks to these characteristics, the apparatus 1 is arranged to carry out a differentiated automatic sorting of both the individual separate packages C and the strips of pre-engraved packages C.

Of course, without prejudice to the principle of the invention, the details of construction and the embodiments may vary widely with respect to those described and illustrated purely by way of example, without departing from the scope of the present invention.

The invention claimed is:

1. A transversal cutting unit for obtaining segments of consecutive articles of desired length from a continuous chain of articles, each segment having engravings between one article and another article of the segment, the transversal cutting unit comprising:
    a cutting roller carrying at least one cutting element configured to perform both a cutting operation to separate two consecutive articles, and an engraving operation between two consecutive articles without separating the two consecutive articles,
    a contrasting roller acting as a cutting surface, wherein a plurality of sections with grooves in the contrasting roller are formed alternating with a plurality of solid sections of the contrasting roller, wherein the contrasting roller is configured for providing segments of consecutive articles of desired length, with engravings between one article and another article of each segment, and
    a control device configured to vary a phase between said cutting roller and said contrasting roller.

2. The unit according to claim 1, wherein said control device is configured to accelerate the contrasting roller with respect to the cutting roller.

3. The unit according to claim 1, wherein said control device is configured to decelerate the contrasting roller with respect to the cutting roller.

4. The unit according to claim 1, wherein said plurality of solid sections and said plurality of sections with grooves are alternated with constant pitch along a circumference of the contrasting roller.

5. A packaging apparatus comprising at least one transversal cutting unit according to claim 1.

6. The apparatus according to claim 5, comprising:
    a forming device configured to fold a packaging film in a form of a continuous envelope surrounding the chain of articles, and
    a transversal welding unit separated and arranged upstream with respect to said at least one transversal cutting unit,
    wherein the welding unit is configured for transversely welding the continuous envelope and the at least one transversal cutting unit is configured for cutting or engraving a welded area of the continuous envelope, and
    wherein the control device is configured to synchronize operations of the welding unit and the at least one transversal cutting unit.

7. The apparatus according to claim 6, comprising:
    a plurality of conveyor means provided for automatically transporting engraved segments of articles to different evacuation points,
    wherein said plurality of conveyor means includes gripping means that are alternatively actuated to direct a predetermined number of segments to each evacuation point.

8. A method for cutting a continuous chain of articles, comprising the following steps:
    feeding the chain of articles along a machine direction,
    providing a transversal cutting unit according to claim 1,
    automatically varying the phase between said cutting roller and said contrasting roller, so as to produce segments of consecutive articles of desired length from the chain of articles, each segment having engravings between one article and another article of the segment.

9. The method according to claim 8, comprising the step of accelerating the contrasting roller with respect to the cutting roller.

10. The method according to claim 8, comprising the step of decelerating the contrasting roller with respect to the cutting roller.

* * * * *

UNITED STATES PATENT AND TRADEMARK OFFICE
CERTIFICATE OF CORRECTION

| | | |
|---|---|---|
| PATENT NO. | : 12,065,278 B2 | Page 1 of 1 |
| APPLICATION NO. | : 18/177664 | |
| DATED | : August 20, 2024 | |
| INVENTOR(S) | : Gabriele Sablone and Antonio Gallucci | |

It is certified that error appears in the above-identified patent and that said Letters Patent is hereby corrected as shown below:

On the Title Page

Item (71) Applicant address information should be listed as:
- Fameccanica.Data S.p.A., San Giovanni Teatino (Chieti), ITALY -

Item (72) Inventor address information should be listed as:
- Gabriele SABLONE, San Giovanni Teatino (Chieti), ITALY
Antonio GALLUCCI San Giovanni Teatino (Chieti), ITALY -

Signed and Sealed this
Twenty-fifth Day of March, 2025

Coke Morgan Stewart
*Acting Director of the United States Patent and Trademark Office*